US008511308B2

(12) United States Patent
Hecox et al.

(10) Patent No.: US 8,511,308 B2
(45) Date of Patent: Aug. 20, 2013

(54) CPR SYSTEM WITH FEED BACK INSTRUCTION

(75) Inventors: Lawrence E. Hecox, Ventura, CA (US); David Eckhous, Long Beach, CA (US); Blain Tomlinson, Long Beach, CA (US)

(73) Assignee: CPaiR, Inc., San Clemente, CA (US)

( * ) Notice: Subject to any disclaimer, the term of this patent is extended or adjusted under 35 U.S.C. 154(b) by 871 days.

(21) Appl. No.: 12/328,652

(22) Filed: Dec. 4, 2008

(65) Prior Publication Data

US 2009/0163838 A1 Jun. 25, 2009

Related U.S. Application Data

(60) Provisional application No. 60/992,842, filed on Dec. 6, 2007, provisional application No. 60/992,855, filed on Dec. 6, 2007.

(51) Int. Cl.
*A62B 7/00* (2006.01)
*A61H 31/00* (2006.01)
*G09B 23/28* (2006.01)

(52) U.S. Cl.
USPC .................. 128/205.23; 128/202.18; 601/41; 434/265; 434/262

(58) Field of Classification Search
USPC ............... 607/4–28; 600/483–485, 500, 502, 600/504, 509, 513, 519, 529, 534, 587; 601/41; 434/265, 262; 128/204.18–207.29, 202.18
See application file for complete search history.

(56) References Cited

U.S. PATENT DOCUMENTS 4,424,814 A 1/1984 Secunda
4,588,383 A * 5/1986 Parker et al. .................. 434/265
4,863,385 A * 9/1989 Pierce .......................... 434/265
5,239,988 A 8/1993 Swanson
5,496,257 A 3/1996 Kelly
5,913,685 A 6/1999 Hutchins
6,213,960 B1 4/2001 Sherman
7,190,999 B2 * 3/2007 Geheb et al. ...................... 607/5
7,289,850 B2 10/2007 Burnes
7,488,293 B2 * 2/2009 Marcovecchio et al. ..... 600/504
7,706,878 B2 * 4/2010 Freeman .......................... 607/6
7,747,319 B2 * 6/2010 Freeman .......................... 607/6
2003/0062040 A1 4/2003 Lurie
2005/0085799 A1 4/2005 Luria
2007/0219588 A1 9/2007 Freeman
2008/0255482 A1 10/2008 Lurie, III
2009/0145430 A1 * 6/2009 Hecox et al. ............. 128/202.28
2009/0145442 A1 * 6/2009 Hecox et al. .................. 128/845

* cited by examiner

*Primary Examiner* — Annette Dixon
(74) *Attorney, Agent, or Firm* — Fish & Associates, PC

(57) ABSTRACT

CPR systems that provide guidance to a CPR provider are presented. Contemplated CPR systems include sensors that collect a victim's biometric data during CPR. The data is processed by an electronic assembly which provides feedback to the CPR provider. The electronic assembly can be packaged within a cranio-cervical extension device having language independent instructions encoded on a surface of the device.

21 Claims, 2 Drawing Sheets

10
150
120
125
130
140
110
160

200
250
260
210
220
240
200
225

CPR SYSTEM WITH FEED BACK INSTRUCTION

This application claims the benefit of priority to U.S. Provisional Application having Ser. No. 60/992,842 and to U.S. Provisional Application having Ser. No. 60/992,855, both filed on Dec. 6, 2007. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is CPR technologies.

BACKGROUND

When a person falls victim to a cardiopulmonary crisis, it is quite likely that trained cardiopulmonary resuscitation (CPR) providers are scarce. Ideally, a nearby person would know CPR and would help the victim. However, in most cases no trained individual is available. Even when a trained provider is available, there is no guarantee the treatment they provide is effective.

CPR requires repeated chest compressions that have to be done correctly to ensure passive return of blood to the heart and proper gas exchange in the lungs. Untrained CPR providers would have a greater success if they could receive instructions quickly on how to proceed and had access to real-time feedback on the effectiveness of the treatment.

U.S. Pat. No. 7,289,850 to Burnes et al. titled "System for Enhanced Cardiac Function with Combined PESP/NES" describes a system where an internal set of sensors are used to determine when cardiac pulse therapy is required for a victim. Although useful for providing feedback for internal medicine, the concepts presented are not applicable to an unexpected emergency situation in a public place, especially when a CPR provider lacks sufficient training.

U.S. Pat. No. 6,213,960 to Sherman et al. titled "Compression Device with Electro-Stimulation" describes a device that has a chest compression mechanism and one or more sensors providing feedback to the device. The described device addresses consistency of compression but is not useable in an emergency by an untrained CPR provider.

U.S. Pat. No. 4,424,814 to Secunda titled "Perfusion Ratio Detector" teaches a perfusion detector that provides a feedback display which is usable by CPR technician or team. Unfortunately the device also requires training and is not easy to use in an emergency because it requires the technician to remove their attention from the victim to observe the feedback.

U.S. Patent Application Publication 2003/0062040 to Lurie et al. titled "Face Mask Ventilation/Perfusion Systems and Method" make further progress in the field by describing a system that can include a headrest and a communication device that allows a CPR provider to obtain instructions from a remote emergency service. However, Lurie fails to provide immediate instruction to a provider.

A preferable CPR system should provide feedback in manner useable by an untrained CPR provider immediately and during CPR and should require a single provider. Thus, there is still a need for providing a system that offers feedback to a CPR provider on the effectiveness of CPR activities as a function of biometric data collected from a victim.

SUMMARY OF THE INVENTION

The present invention provides apparatus, systems and methods in which a CPR provider receives feedback on the effectiveness of their actions as a function of biometric data.

One aspect of the inventive subject matter includes a system that provides guidance to a CPR provider during CPR. The system includes a sensor that acquires biometric data from a victim. An electronic assembly, preferably disposed within a cavity of a cranio-cervical extension device, collects the biometric data from one or more sensors and supplies feedback to the provider as a function of the data. The system can also include the cranio-cervical extension device that provides proper capital extension to open the victim's air passage when placed beneath the victim's neck, preferably sized and dimensions as a saddle shaped pillow. In preferred embodiments, the device includes instructions as least partially encoded on the surface of the device to give immediate guidance to the CPR provider on the use of the system. The instructions can be a language independent icon molded into a surface of the device.

Preferred embodiments of the system utilize a perfusion sensor that collects blood flow data from the victim. During CPR the blood flow data is used to determine the effectiveness of the provider's CPR methods. The electronic assembly collects the blood flow data and advises the CPR provider on how to modify their tactics to increase the effectiveness of the CPR procedures. Especially preferred embodiments employ audible feedback to the provider.

Various objects, features, aspects and advantages of the inventive subject matter will become more apparent from the following detailed description of preferred embodiments, along with the accompanying drawings in which like numerals represent like components.

DETAILED DESCRIPTION

A preferred CPR system includes a cranio-cervical extension device, one or more sensors including a perfusion sensor, and an electronic assembly that collects biometric data from the sensors.

Cranio-cervical extension devices help to ensure that a victim's air passage is open and receptive to air flow. Preferred devices include saddle shaped pillows that are placed beneath the victim's neck. The shape of the pillow causes proper capital extension of the victim's carnio-cervical area for improved air flow without requiring the provider to be trained in proper positioning of the victim. A preferred device is described more fully in co-owned U.S. patent application Ser. No. 12/327,363 titled "Cranio-Cervical Extension Pillow with Dual Arcs".

Figure 1:
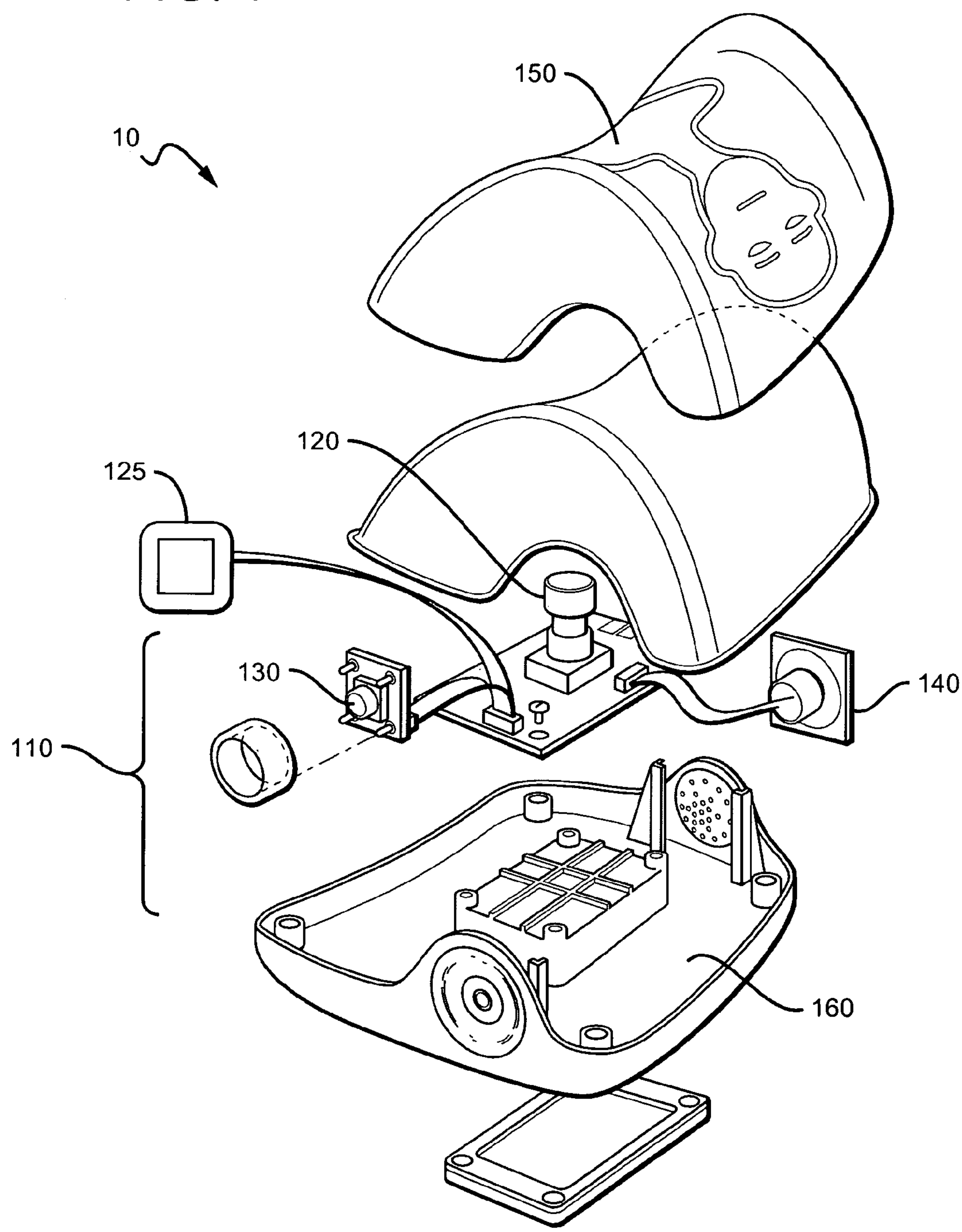
FIG. 1. is a schematic of a CPR system embodied as a CPR kit.

In FIG. 1, provides an exploded view of a cranio-cervical extension device in the form of pillow 100. Pillow 100 (also referred to as "device 100") forms a housing that defines cavity 160, in which is disposed electronic assembly 110. Preferred device 100 includes power button 130, possibly placed on a lateral side of the device 100 for easy access.

Preferably, device 100 also includes speaker 140 to provide audio feedback to a CPR provider. In a preferred embodiment, device 100 also includes one or more of sensors 120 or 125.

Preferred device 100 include instructions to the CPR provider by at least partially encoding the instruction on a surface of the device. Preferably the instructions comprise one or more of language independent icon 150. In the example show, icon 150 illustrates the proper positioning of a victim on the device. Instructions are preferably molded into the surface, possibly as a raise rib. Other icons can include indications of where the power button is located, a numbered sequence of steps, locations of sensors, or other instructions. Providing instructions on the surface of device 100 provides immediate guidance to the CPR provider upon accessing device 100 without requiring reading a manual or contacting a trained profession.

Preferably, cavity 160 has sufficient volume for packaging the various components of a CPR system or kit. For example, the device can include slots for storing one or more of sensors 120 or 125, a space for an internal electronic assembly, an air source, or other CPR related items.

Sensor 125 preferably includes a perfusion sensor to collect blood flow data while the CPR provider performs CPR. In a preferred embodiment, a perfusion sensor 125 couples to an electronic assembly 110 within cranio-cervical extension device 100. Sensor 125 can be at least partially coated with an adhesive so the sensor can couple to a cranio-cervical surface of the victim. Any suitable perfusion sensor can be used if it can acquire data from a victim, preferably from the neck area. A suitable perfusion sensor is described in U.S. Pat. No. 4,424,814 to Secunda.

It is also contemplated that additional sensors beyond a perfusion sensor can be included in a CPR kit. Contemplated additional sensors include temperature, oxygen, $CO_2$, pulse-wave, compression, or other biometric sensors. For example, sensor 120 could comprise a compression sensor placed at the saddle point. In some embodiments, the compression sensor can be a load switch that gathers force data. It is also contemplated that sensor 120 could operate as power button 130.

In some embodiments each of sensors 125 can be formed to have a different shape (e.g., triangle, square, rectangle, pentagon, circle, etc.) so an untrained CPR provider can quickly and easily distinguish the sensors from each other. In such embodiments, the surface of device 100 can be encoded with sensor placement instructions showing the proper location of where each sensor should be placed on the victim. Each placement instruction could be represented by an icon having a shape or other representation corresponding to the actual sensor.

A preferred electronic assembly 110 acquires biometric data from sensors 125 or 120 and processes the data to determine the effectiveness of the CPR provider's methods. The electronic assembly comprises a memory storing software instruction or data, and a processing unit that executes the software instruction. The assembly's roles and responsibilities will be discussed in greater detail below.

Once power is supplied to the assembly 110 and sensors are attached to the victim, the electronics are able to collect biometric data from sensors 125 or 120. Assembly 110 can also provide audible instructions to the CPR provider as a function on the data collected. In the preferred embodiment, instructions take the form of real-time audible feedback. Providing audible feedback allows the provider to keep their attention focused on the victim rather than turning their head to view a visual display.

Contemplated audible feedback includes verbal feedback where a voice indicates how well the provider is performing. For example, if a perfusion sensor 125 data indicates that the victim's blood flow is poor, the voice could state "Please provide stronger compression strokes". Alternatively, if the sensor data indicates that the blood flow is acceptable, the voice could state "Good job. Please continue compression strokes."

It is also contemplated that the feedback can comprise non-verbal feedback. For example, the electrical assembly 110 in FIG. 1 could supply a metronome that indicates the rate at which the provider should do compressions. In some embodiments, the volume of the metronome could indicate if the compression strokes should be harder or softer. Additionally, feedback could include visual feedback in the form of colored lights, preferably lighting the sides of device 100 to reduce risk of causing the provider to become distracted.

Figure 2:
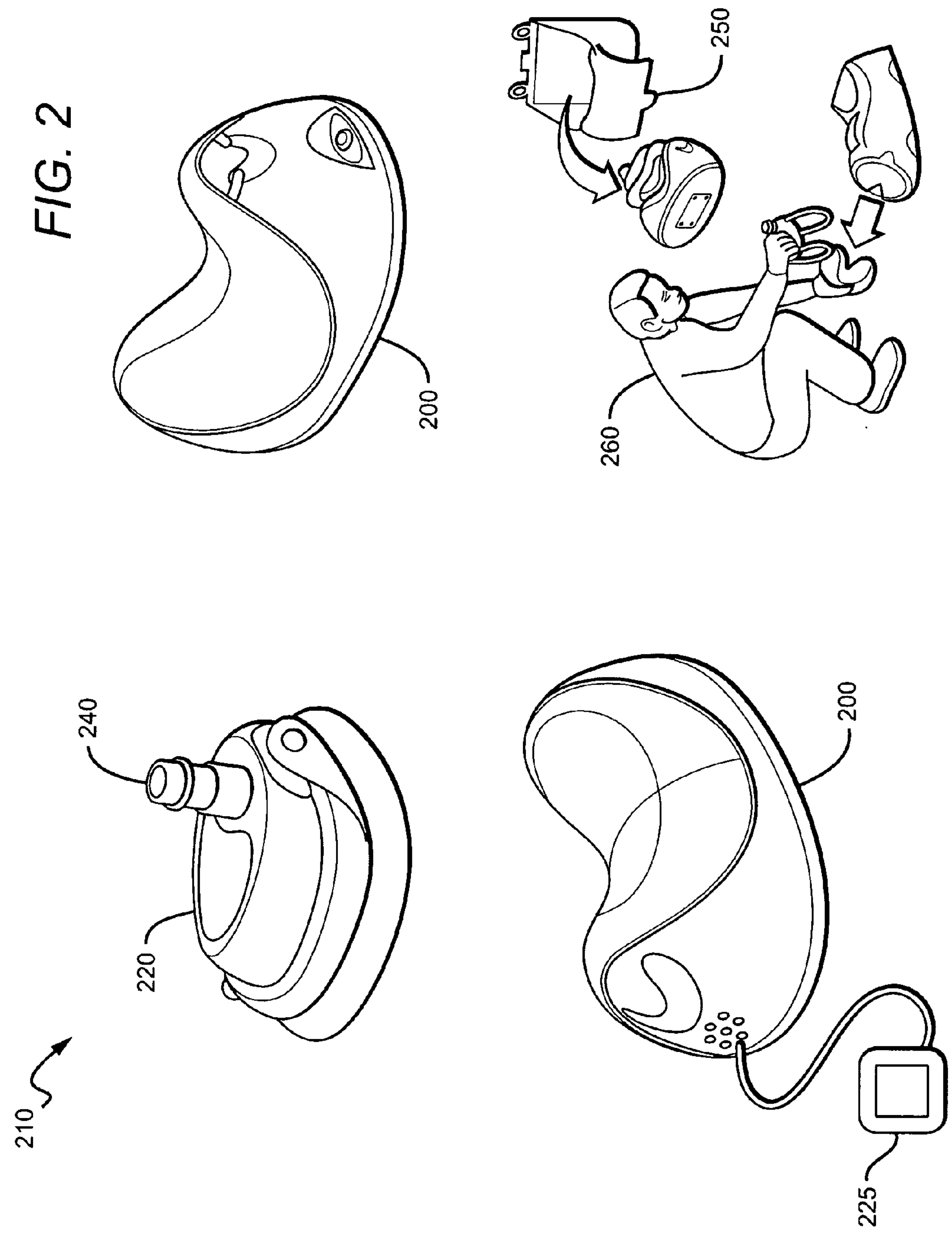
FIG. 2. is a schematic of an exploded view of a cranio-cervical extension pillow housing an electronic assembly.

In FIG. 2, the contemplated CPR system is embodied by a CPR kit 210 as shown in different views. Kit 210 preferably is placed in public locations including schools, transportation hubs, commercial venues, or other places where people congregate. Wall Mounted CPR Kit 250 can be mounted on a publicly accessible wall, for example, where CPR provider 260 can quickly access the kit when an emergency arises.

Beyond cranio-cervical extension devices 200, sensors 225, and electronics, CPR kits 210 are also contemplated to include additional items to aid a CPR provider while helping the victim. The additional items can include breathing mask 220, an air source (not shown), instructions, or other items.

Masks 220 can be coupled to pillow device 200 via straps or more preferably could be strapless as shown. A strapless mask 220 could couple to a victim's face using a sticky or tacky gasket seal. Providing a strapless mask allows the CPR provider to quickly place the mask on the victim's face or remove the mask quickly should the need arise. For example, if the victim vomits, the provider can remove mask 220 and quickly clean the victim's air passage to prevent choking. All ventilation, resuscitation, or respiration masks are contemplated including those with straps or without straps.

In some embodiments, mask 220 is adapted with a gas source input 240. Gas source input 240 allows a gas, including air, to flow from a gas source through the victim's air passage to their lungs. For example, mask 220 could include a port (as shown) in which provider 260 blows air to provide air to the victim's lungs. It is also contemplated that the CPR kit 210 could include a readily available air source for use by the provider including a pump, a pressurized tank, an air bag, or other gas sources.

Preferred kits 210 are packaged in manner where all elements of the kit are easily accessible, while utilizing a small volume. As previously mentioned, a cranio-cervical extension device associated with the kit preferably has a cavity in which various items of the kit can be disposed. It is contemplated, that mask 220, air source, electronics, sensors 125, or other equipment can be placed within the device. Keeping the kit small allows the kit to be placed in confined spaces including within emergency vehicles, air planes, cars, backpacks, or other places where space is at a premium.

Preferred kits also include one or more instructions for the provider. Especially preferred kits have instructions encoded on the surface of the kits items. For example, instructional icon 150 in FIG. 1 shows an icon of a person molded on to the surface of the cranio-cervical extension device indicating how to properly position the victim. Visual icons on the kit items allow a CPR provider to place the items quickly without having to consult a manual. Additionally, preferred instructions can also be provided verbally from the electronic assembly.

Other embodiments are also responsive to voice commands from provider 260. As the electrical assembly provides instructions to provider 260, occasionally decision points are reached where the unit could require input from provider 260. Provider 260 inputs data to the electrical assembly by vocalizing their directives or choices rather than removing their attention from the victim. Consider a case where the instructions provided by the assembly could change based on the age of the victim. The assembly could ask "Is the victim a baby, a child, or an adult? Please speak your answer"; provider 260 can then respond with any of the choices. The assembly could then provide proper instruction for the specific case or alter its interpretation of the sensor data.

In some embodiments, sensor information is communicated using a telemetry unit (not show) which contacts remote personnel that can aid the provider in helping to care for the victim. Contemplated telemetry units include cell phones, network connections (e.g. wired or wireless) or other communication units that can otherwise offer communication methods. Telemetry units can include cell phone transceivers responsive to CDMA, GSM, or other carrier signals. Additionally, telemetry unit could include a transceiver responsive to 802.11, 802.15, 802.15, or other wireless network signals.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system that provides guidance to a CPR provider during CPR of a victim; the system comprising:

a cranio-cervical extension device comprising a pillow having a shape that opens a victim's air passage when the pillow is disposed under the victim's neck and having language independent instructions at least partially encoded on a surface of the device;

a first biometric sensor that acquires a first type of biometric data from the victim;

a second biometric sensor that acquires a second type of biometric data from the victim;

wherein the first type of biometric data is different than the second type of biometric data; and an electronic assembly disposed within the device that provides feedback to the provider as a function of the biometric data.

2. The system of claim 1, wherein the feedback is audible.

3. The system of claim 2, wherein the audible feedback comprises a metronome.

4. The system of claim 2, wherein the audible feedback comprises a voice.

5. The system of claim 1, wherein the feedback instructs the provider to use a stronger compression stroke.

6. The system of claim 1, wherein the feedback instructs the provider that the provider is using an adequate compression stroke.

7. The system of claim 1, wherein the pillow has a saddle shape.

8. The system of claim 1, wherein the first biometric sensor is packaged within the device.

9. The system of claim 1, wherein the first biometric sensor comprises a perfusion sensor that acquires blood flow data.

10. The system of claim 1, further comprising an adhesive disposed to couple the first biometric sensor to a cranio-cervical surface of the victim.

11. The system of claim 1, further comprising a a third biometric sensor that acquires a third type of biometric data from the victim.

12. The system of claim 11, wherein the third biometric sensor includes at least one of the following: a compression sensor, an oxygen sensor; CO2 sensor; a pulse wave sensor; and a temperature sensor.

13. The system of claim 1, further comprising a breathing mask adapted to provide air from an air source and to fit over the victim's nose and mouth.

14. The system of claim 13, further comprising the air source packaged with the device.

15. The system of claim 14, wherein the air source comprises at least one of the following: a bag; a pressurized tank; and a pump.

16. The system of claim 14, wherein the air source is packaged within the device.

17. The system of claim 13, wherein the mask is strapless.

18. The system of claim 1, wherein the instructions comprise an icon.

19. The system of claim 18, wherein the icon is molded into the surface.

20. The system of claim 1, wherein the electronic assembly is adapted to respond to a voice command from the provider.

21. The system of claim 1, further comprising a telemetry unit.

* * * * *